United States Patent
Perron et al.

(10) Patent No.: US 7,179,770 B2
(45) Date of Patent: Feb. 20, 2007

(54) DETERGENT COSMETIC COMPOSITIONS COMPRISING A POLYMER MIXTURE, FOR CLEANING, CONDITIONING AND STYLING KERATINOUS FIBERS

(75) Inventors: Béatrice Perron, Jouy En Josas (FR); Serge Restle, Saint-Prix (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/499,019

(22) PCT Filed: Dec. 18, 2002

(86) PCT No.: PCT/FR02/04438

§ 371 (c)(1), (2), (4) Date: Feb. 23, 2005

(87) PCT Pub. No.: WO03/053382

PCT Pub. Date: Jul. 3, 2003

(65) Prior Publication Data

US 2005/0130871 A1 Jun. 16, 2005

(51) Int. Cl.
*C11D 3/37* (2006.01)
*C11D 9/36* (2006.01)

(52) U.S. Cl. ............... 510/124; 510/119; 510/122; 510/434; 510/477; 510/504; 510/466

(58) Field of Classification Search ............ 510/119, 510/122, 124, 434, 477, 504, 466
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 4,240,450 A * | 12/1980 | Grollier et al. | 132/209 |
| 4,304,563 A * | 12/1981 | Grollier et al. | 8/127.51 |
| 4,381,259 A * | 4/1983 | Homma et al. | 510/122 |
| 4,772,462 A * | 9/1988 | Boothe et al. | 510/123 |
| 4,839,166 A | 6/1989 | Grollier et al. | |
| 4,867,971 A * | 9/1989 | Ryan et al. | 514/399 |
| 4,895,722 A * | 1/1990 | Abe et al. | 424/70.14 |
| 5,124,078 A * | 6/1992 | Baust | 510/124 |
| 5,275,755 A * | 1/1994 | Sebag et al. | 510/121 |
| 5,310,508 A * | 5/1994 | Subramanyam et al. | 510/127 |
| 5,567,428 A * | 10/1996 | Hughes | 424/401 |
| 5,665,337 A * | 9/1997 | Carballada et al. | 424/70.12 |
| 5,726,137 A * | 3/1998 | Patel et al. | 510/122 |
| 5,965,115 A * | 10/1999 | Bolich et al. | 424/70.12 |
| 5,977,036 A | 11/1999 | Guskey | |
| 6,022,836 A | 2/2000 | Dubief et al. | |
| 6,423,305 B1 | 7/2002 | Cauwet-Martin et al. | |
| 6,534,455 B1 | 3/2003 | Maurin et al. | |
| 6,555,117 B2 * | 4/2003 | Midha et al. | 424/401 |
| 2003/0021758 A1 * | 1/2003 | Cannell et al. | 424/70.13 |
| 2003/0086886 A1 * | 5/2003 | Midha et al. | 424/70.2 |

FOREIGN PATENT DOCUMENTS

| | | |
|---|---|---|
| EP | 1 090 633 A | 11/2001 |
| FR | 2 589 476 A | 10/1985 |
| FR | 2 598 611 A | 5/1987 |
| FR | 2 736 262 A | 7/1995 |
| FR | 2 750 047 A | 6/1996 |
| FR | 2 773 069 A | 12/1997 |
| WO | WO 99/13837 A1 | 3/1999 |
| WO | WO 00/37041 A1 | 6/2000 |
| WO | WO 01/12153 A1 | 2/2001 |
| WO | WO 01/17500 A1 | 3/2001 |

OTHER PUBLICATIONS

English language Derwent Abstract of FR 2 750 047 A.
English language Derwent Abstract of FR 2 589 476 A.
International Search Report in PCT/FR02/04438, dated Apr. 17, 2003.

* cited by examiner

*Primary Examiner*—Charles Boyer
(74) *Attorney, Agent, or Firm*—Finnegan, Henderson, Farabow, Garrett and Dunner L.L.P.

(57) ABSTRACT

The invention concerns novel washing compositions in particular for the hair, comprising, in a cosmetically acceptable medium, at least a detergent surfactant, at least a polymer comprising at least a dialkyldiallylammonium monomer and at least a adhesive polymer having a glass transition temperature less than −20° C. Said compositions have enhanced hair styling effect.

25 Claims, No Drawings

DETERGENT COSMETIC COMPOSITIONS COMPRISING A POLYMER MIXTURE, FOR CLEANING, CONDITIONING AND STYLING KERATINOUS FIBERS

This application is a national stage application from International Application No. PCT/FR02/04438, filed Dec. 18, 2002, which claims priority to French Application No. FR 01/16582, filed Dec. 20, 2001, all of which are hereby incorporated by reference.

The present invention relates to novel cosmetic compositions with improved properties intended simultaneously for cleansing, conditioning and styling keratin materials, especially the hair, and comprising, in a cosmetically acceptable support, a washing base consisting of surfactants with detergent power, in which are also present particular cationic or amphoteric polymers in combination with adhesive polymers with a glass transition temperature of less than −20° C. The invention also relates to the use of said compositions in the abovementioned cosmetic application.

It is common practice to use detergent hair compositions (or shampoos) based essentially on standard surfactants especially of anionic, nonionic and/or amphoteric type, but more particularly of anionic type, to cleanse and/or wash the hair. These compositions are applied to wet hair and the lather generated by massaging or rubbing with the hands allows, after rinsing with water, the removal of the various types of soiling initially present on the hair.

These base compositions do indeed have good washing power, but the intrinsic cosmetic properties associated therewith are, however, relatively poor, especially due to the fact that the relatively aggressive nature of such a cleansing treatment can result in more or less pronounced damage to the hair fibers in the long run, which is associated in particular with the gradual removal of the lipids or proteins contained in or at the surface of these fibers.

Thus, to improve the cosmetic properties of the above detergent compositions, and more particularly of those intended to be applied to sensitized hair (i.e. hair that is in a damaged or embrittled condition, especially due to the chemical action of atmospheric agents and/or hair treatments such as permanent-waving, dyeing or bleaching operations), it is now common practice to introduce into these compositions additional cosmetic agents known as conditioners, which are mainly intended to repair or limit the harmful or undesirable effects induced by the various treatments or attacking factors to which hair fibers are more or less repeatedly subjected. These conditioners can, of course, also improve the cosmetic behavior of natural hair.

The conditioners most commonly used to date in shampoos are cationic polymers, which give washed, dry or wet hair markedly increased ease of disentangling, softness and smoothness when compared with that which may be obtained with the corresponding conditioner-free cleansing compositions.

Moreover it has been sought for some time to obtain conditioning shampoos that are capable of giving washed hair not only the cosmetic properties mentioned above, but also, to a greater or lesser degree, styling, volume, shaping and hold properties. The latter washing shampoos with improved general cosmetic properties are often referred to for simplicity as "styling shampoos", and this term will be adopted in the description hereinbelow.

However, despite the progress recently made in the field of styling shampoos, these products do not truly give total satisfaction, and as such there is currently still a strong need to provide novel products that show better performance properties as regards one or more of the cosmetic properties mentioned above.

The present invention is directed toward satisfying such a need.

Thus, after considerable research conducted in this matter, the Applicant has now found, entirely surprisingly and unexpectedly, that by combining particular cationic or amphoteric polymers, as defined below, with certain polymers with a glass transition temperature of less than −20° C. and having a particular adhesive power, in detergent compositions, it is possible to substantially and significantly improve the cosmetic properties associated with these compositions, while at the same time conserving their good intrinsic washing power.

These compositions especially make it possible to obtain good hold and a certain degree of volume for the hair, i.e. a styling effect. It is moreover found that the keratin fibers are hardened and reinforced.

Without wishing to limit the present invention to any theory, it would appear that, between the cationic or amphoteric polymers, the adhesive polymers in accordance with the invention and the hair, there are particular interactions and/or affinities that promote a regular, sizable and long-lasting deposition of said adhesive polymers at the surface of said hair, this qualitative and quantitative deposition probably being one of the causes of the improvement observed as regards the final cosmetic properties, in particular the ease of styling, the hold, the liveliness and the volume of the treated hair. In any case, the cosmetic properties associated with the detergent compositions containing the combination of agents [cationic or amphoteric polymer comprising at least one diallyldialkylammonium monomer/adhesive polymer] in accordance with the invention are markedly better than those that may be obtained by using the adhesive polymer and a different cationic polymer.

All these discoveries form the basis of the present invention.

Thus, according to the invention, novel compositions for washing keratin materials, in particular the hair, are now proposed, these compositions comprising, in cosmetically acceptable aqueous medium, at least one adhesive polymer with a glass transition temperature of less than −20° C., at least one cationic or amphoteric polymer comprising at least one diallyldialkylammonium monomer, and at least one detergent surfactant.

A subject of the invention is also the use of a cationic or amphoteric polymer comprising at least one diallyldialkylammonium monomer to improve the styling effect of a composition containing at least one adhesive polymer.

A subject of the invention is also the cosmetic use of the above compositions for cleansing, conditioning, caring for and styling keratin materials, especially the hair and the eyelashes.

Another subject of the invention consists of a cosmetic process for treating keratin materials, especially keratin fibers and more particularly the hair and the eyelashes, using the composition according to the invention.

A subject of the invention is also the use of he composition according to the invention as a shampoo.

However, other characteristics, aspects and advantages of the invention will emerge even more clearly on reading the description that follows, and also the concrete, but in no way limiting, examples intended to illustrate it.

The term "adhesive polymer" more particularly denotes a polymer with a maximum tensile force Fmax of greater than 2 newtons, preferably between 5 and 100 N and more particularly between 7 and 35 newtons.

According to the present invention, the term "maximum peel force Fmax" means the maximum tensile force, measured using an extensometer (Lloyd L5K from Lloyd Instrument) required to detach the surfaces of 95 mm$^2$ of two rigid, inert, nonabsorbent supports (A) and (B) respectively, placed facing each other; said surfaces being precoated with a formulation consisting of the adhesive polymer(s) in water, at a rate of 53/c μg/mm$^2$, dried for 48 hours at 22° C., under a relative humidity of 55%, and then subjected for 20 seconds to a compression of 3 newtons and finally subjected for 30 seconds to a tension at a speed of 20 mm/minute, c being the solids concentration in the formulation consisting of the adhesive polymer(s) in water, expressed as grams per gram of composition.

Circular supports (A) and (B) consisting of polyethylene, polypropylene, metal alloy and, preferably, glass, are preferably used.

The glass transition temperature is measured by differential thermal analysis.

To measure the glass transition temperature, a film of the test polymer about 150 microns thick is made by depositing an aqueous solution or dispersion of the polymer into a circular Teflon mold 40 mm in diameter and leaving the deposit to dry. The film is dried in an oven at a temperature of about 23° C. under a relative humidity of 45%, until the weight no longer changes. 5 to 15 mg of the film are taken, and placed in a crucible, which is then introduced into the analyzer. The thermal analyzer is a DSC-2920 model from TA-Instrument. The initial and final temperatures are chosen so as to flank the desired glass transition temperature, with a temperature sweep speed of 10° C./minute.

This analysis is performed according to ASTM standard D 3418-97 with the exception of the above modifications.

The adhesive polymers according to the invention preferably have a glass transition temperature of between –100° C. and –20° C. and more particularly between –70° C. and –25° C.

Among the adhesive polymers of the invention that may particularly be mentioned are acrylic acid copolymers, especially those known as CARBOTAC XPD-1811 sold by the company Noveon (Tg of about –43° C. and maximum peel force $F_{max}$ equal to about 11.2 newtons) and Carbotac XPD-1814 (Tg=–30° C.).

The comonomers are especially $C_1$–$C_4$ alkyl (meth)acrylates, acrylamide, methacrylamide and acrylonitrile.

Examples of copolymers that may be used include copolymers of acrylic acid, of acrylamide, of ethyl acrylate and of acrylonitrile, such as the products known as Hystretch V29 (Tg=–29° C.), Hystretch V43 (Tg=–43° C.) and Hystretch V60 (Tg=–60° C.).

The polymers are especially in the form of a dispersion or emulsion in water. The mean size of the polymer particles in the dispersion is generally between 5 and 500 nm and preferably between 15 and 250 nm.

The adhesive polymers are present in the compositions of the invention at a concentration of between 0.05% and 20% by weight, preferably between 0.1% and 10% and more particularly between 0.5% and 5% by weight relative to the total weight of the composition.

The detergent surfactant(s) may be chosen, without preference, alone or as mixtures, from anionic, amphoteric, nonionic, zwitterionic and cationic surfactants.

Thus, according to the invention, the detergent surfactants may represent from 4% to 50% by weight, preferably from 6% to 25% by weight and even more preferably from 8% to 20% by weight relative to the total weight of the final composition.

The surfactants that are suitable for use in the present invention are especially the following:

(i) Anionic Surfactant(s):

In the context of the present invention, their nature is not a truly critical feature.

Thus, as examples of anionic surfactants that can be used, alone or as mixtures, in the context of the present invention, mention may be made in particular (nonlimiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Weakly anionic surfactants can also be used, such as alkyl-D-galactosiduronic acids and their salts, as well as polyoxyalkylenated ether carboxylic acids and their salts, in particular those containing from 2 to 50 ethylene oxide groups, and mixtures thereof.

The anionic surfactants of the polyoxyalkylenated carboxylic ether acid or salt type are in particular those corresponding to formula (1) below:

$$R_1\text{—}(OC_2H_4)_n\text{—}OCH_2COOA \qquad (1)$$

in which:

$R_1$ denotes an alkyl, alkylamido or alkaryl group and n is an integer or fractional number (mean value) that can range from 2 to 24 and preferably from 3 to 10, the alkyl radical containing between 6 and 20 carbon atoms approximately, and aryl preferably denoting phenyl.

A denotes H, ammonium, Na, K, Li, Mg or a monoethanolamine or triethanolamine residue. Mixtures of compounds of formula (1) and in particular mixtures in which the groups $R_1$ are different may also be used.

Compounds of formula (1) are sold, for example, by the company Chem Y under the names Akypos (NP 40, NP 70, OP 40, OP 80, RLM 25, RLM 38, RLMQ 38 NV, RLM 45, RLM 45 NV, RLM 100, RLM 100 NV, RO 20, RO 90, RCS 60, RS 60, RS 100, RO 50) or by the company Sandoz under the name Sandopan (DTC Acid, DTC).

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (nonlimiting list) polyethoxylated, polypropoxylated or polyglycerolated fatty acids, alkylphenols, α-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides. It will be noted that the alkylpolyglycosides constitute nonionic surfactants that are particularly suitable for use in the context of the present invention.

(iii) Amphoteric or Zwitterionic Surfactant(s):

The amphoteric or zwitterionic surfactants, whose nature is not a critical feature in the context of the present invention, can be, in particular (nonlimiting list), aliphatic secondary or tertiary amine derivatives in which the aliphatic radical is a linear or branched chain containing 8 to 18 carbon atoms and containing at least one water-soluble anionic group (for example carboxylate, sulfonate, sulfate, phosphate or phosphonate); mention may also be made of ($C_8$–$C_{20}$)alkylbetaines, sulfobetaines, ($C_8$–$C_{20}$)alkylamido($C_1$–$C_6$)alkylbetaines or ($C_8$–$C_{20}$)alkylamido($C_1$–$C_6$) alkylsulfobetaines.

Among the amine derivatives, mention may be made of the products sold under the name Miranol, as described in U.S. Pat. Nos. 2,528,378 and 2,781,354, and classified in the CTFA dictionary, 3rd Edition, 1982, under the names Amphocarboxyglicinates and Amphocarboxypropionates, and having the respective structures:

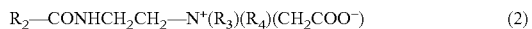

$$R_2\text{—CONHCH}_2\text{CH}_2\text{—N}^+(R_3)(R_4)(CH_2COO^-) \quad (2)$$

in which: $R_2$ denotes an alkyl radical derived from an acid $R_2$—COOH present in hydrolyzed coconut oil, a heptyl, nonyl or undecyl radical, $R_3$ denotes a β-hydroxyethyl group and $R_4$ denotes a carboxymethyl group;

and

$$R_2'\text{—CONHCH}_2\text{CH}_2\text{—N(B)(C)} \quad (3)$$

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_2'$ denotes an alkyl radical of an acid $R_9$—COOH present in coconut oil or in hydrolyzed linseed oil, an alkyl radical, in particular a $C_7$, $C_9$, $C_{11}$, or $C_{13}$ alkyl radical, a $C_{17}$ alkyl radical and its iso form, an unsaturated $C_{17}$ radical.

An example that may be mentioned is cocoamphocarboxyglycinate sold under the trade name Miranol C2M concentrate by the company Miranol.

(iv) Cationic Surfactants:

Among the cationic surfactants that may be mentioned in particular are (nonlimiting list): optionally polyoxyalkylenated primary, secondary or tertiary fatty amine salts; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

It will be noted that the cationic surfactants, the use of which is not excluded, do not constitute preferred surfactants for use in the present invention.

The polymers comprising at least one dialkyldiallylammonium monomer are especially homopolymers or copolymers comprising, as chain constituents, at least one unit corresponding to the formula (4a) or (4b):

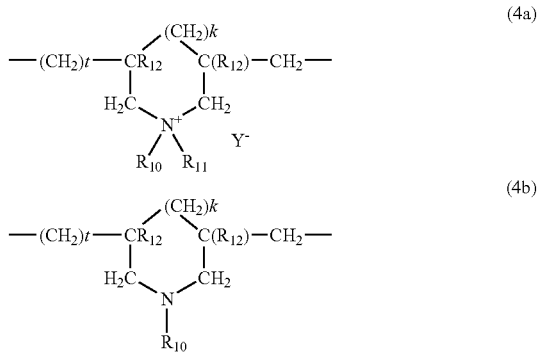

in which k and t are equal to 0 or 1, the sum k+t being equal to 1; $R_{12}$ denotes a hydrogen atom or a methyl group; $R_{10}$ and $R_{11}$, independently of each other, denote an alkyl group containing from 1 to 8 carbon atoms, a hydroxyalkyl group in which the alkyl group preferably contains 1 to 5 carbon atoms, or a lower ($C_1$–$C_4$)amidoalkyl group, or alternatively $R_{10}$ and $R_{11}$ may denote, together with the nitrogen atom to which they are attached, heterocyclic groups such as piperidyl or morpholinyl; $Y^-$ is an anion such as bromide, chloride, acetate, borate, citrate, tartrate, bisulfate, bisulfite, sulfate or phosphate. These polymers are described especially in French patent 2 080 759 and in its certificate of addition 2 190 406.

$R_{10}$ and $R_{11}$, independently of each other, preferably denote an alkyl group containing from 1 to 4 carbon atoms.

Among the polymers defined above, mention may be made more particularly of the dimethyldiallylammonium salts (especially the chloride) sold under the name "Merquat® 100" by the company Nalco (and the homologues thereof of low molecular mass). It is also possible to use the copolymers of dimethyldiallylammonium salts (especially the chloride) and of acrylamide sold under the names Merquat® 100, and Merquat® 550 by the company Nalco, and the copolymers of dimethyldiallylammonium salts (especially the chloride) and of acrylic acid sold under the names Merquat® 280 and Merquat® 295 by the company Nalco.

Preferably, the composition according to the invention may contain one or more cationic or amphoteric polymers as described above, in an amount ranging from 0.001% to 10% by weight and preferably from 0.05% to 5% by weight relative to the total weight of the composition.

The cationic polymer may be used in a weight ratio with the adhesive polymer of between 100 and 0.0005, preferably between 20 and 0.01 and even more particularly between 1 and 0.05.

According to one preferred mode of the invention, the compositions may also comprise at least one silicone.

Among the silicones that may be used in the composition of the present invention, mention may be made especially of volatile or nonvolatile, cyclic or acyclic, branched or unbranched, organomodified or non-organomodified silicones, as described below.

The silicones that may be used in accordance with the invention may be soluble or insoluble in the composition and in particular may be polyorganosiloxanes that are insoluble in the composition of the invention; they may be in the form of oils, waxes, resins or gums.

According to the invention the silicones may all be used in unmodified form or in the form of solutions, dispersions, emulsions, nanoemulsions or microemulsions.

The organopolysiloxanes are defined in greater detail in Walter Noll's "Chemistry and Technology of Silicones" (1968) Academic Press. They can be volatile or nonvolatile.

When they are volatile, the silicones are more particularly chosen from those having a boiling point of between 60° C. and 260° C., and even more particularly from:

(i) cyclic silicones containing from 3 to 7 and preferably 4 to 5 silicon atoms. These are, for example, octamethylcyclotetrasiloxane sold in particular under the name "Volatile Silicone 7207" by Union Carbide or "Silbione 70045 V 2" by Rhodia, decamethylcyclopentasiloxane sold under the name "Volatile Silicone 7158" by Union Carbide, and "Silbione 70045 V 5" by Rhodia, and mixtures thereof.

Mention may also be made of cyclocopolymers of the dimethylsiloxane/methylalkylsiloxane type, such as "Silicone Volatile FZ 3109" sold by the company Union Carbide, having the chemical structure:

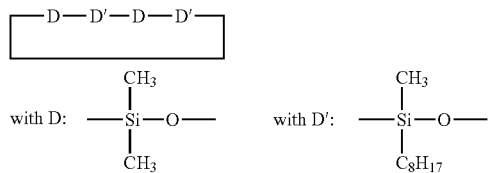

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'—bis (2,2,2',2',3,3'-hexatrimethylsilyloxy)neopentane;

(ii) linear volatile silicones containing 2 to 9 silicon atoms and having a viscosity of less than or equal to $5\times10^{-6}$ m$^2$/s at 25° C. An example is decamethyltetrasiloxane sold in particular under the name "SH 200" by the company Toray Silicone. Silicones belonging to this category are also described in the article published in Cosmetics and Toiletries, Vol. 91, Jan. 76, pp. 27–32, Todd & Byers "Volatile Silicone Fluids for Cosmetics".

Nonvolatile silicones, and more particularly polyalkylsiloxanes, polyarylsiloxanes, polyalkylarylsiloxanes, silicone gums and resins, polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups having a viscosity of from $5\times10^{-6}$ to 2.5 m$^2$/s at 25° C. and preferably $1\times10^{-5}$ to 1 m$^2$/s. The viscosity of the silicones is, for example, measured at 25° C. according to ASTM standard 445 Appendix C.

Among these polyalkylsiloxanes, mention may be made, in a nonlimiting manner, of the following commercial products:

the Silbione® oils of the 47 and 70 047 series or the Mirasil® oils sold by Rhodia such as, for example, the oil 70 047 V 500 000;

the oils of the Mirasil® series sold by the company Rhodia;

the oils of the 200 series from the company Dow Corning, such as, more particularly, DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhodia Chimie.

In this category of polyalkylsiloxanes, mention may also be made of the products sold under the names "Abil Wax® 9800 and 9801" by the company Goldschmidt, which are poly($C_1$–$C_{20}$)alkylsiloxanes.

The polyalkylarylsiloxanes are chosen particularly from linear and/or branched polydimethylmethylphenylsiloxanes or polydimethyldiphenylsiloxanes, with a viscosity of from $1\times10^{-5}$ to $5\times10^{-2}$ m$^2$/s at 25° C.

Among these polyalkylarylsiloxanes, mention may be made, by way of example, of the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250, SF 1265.

The silicone gums that can be used in accordance with the invention are, in particular, polydiorganosiloxanes having high number-average molecular masses of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:

polydimethylsiloxane,
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Products that can be used more particularly in accordance with the invention are mixtures such as:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs of different viscosities, and more particularly of a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of $5 \times 10^{-6}$ m²/s. This product preferably contains 15% SE 30 gum and 85% SF 96 oil.

The organopolysiloxane resins that can be used in accordance with the invention are crosslinked siloxane systems containing the following units:

$R_2SiO_{2/2}$, $R_3SiO_{1/2}$, $RSiO_{3/2}$ and $SiO_{4/2}$ in which R represents a hydrocarbon-based group containing 1 to 16 carbon atoms or a phenyl group. Among these products, those particularly preferred are the ones in which R denotes a $C_1$–$C_4$ lower alkyl radical, more particularly methyl, or a phenyl radical.

Among these resins, mention may be made of the product sold under the name "Dow Corning 593" or those sold under the names "Silicone Fluid SS 4230 and SS 4267" by the company General Electric, which are silicones of dimethyl/trimethylsiloxane structure.

Mention may also be made of the trimethyl siloxysilicate type resins sold in particular under the names X22-4914, X21-5034 and X21-5037 by the company Shin-Etsu.

The organomodified silicones that can be used in accordance with the invention are silicones as defined above and containing in their structure one or more organofunctional groups attached via a hydrocarbon-based group.

Among the organomodified silicones, mention may be made of polyorganosiloxanes comprising:

polyethyleneoxy and/or polypropyleneoxy groups optionally comprising $C_6$–$C_{24}$ alkyl groups, such as the products known as dimethicone copolyol sold by the company Dow Corning under the name DC 1248 or the oils Silwet® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, in particular, $C_1$–$C_4$ aminoalkyl groups;

thiol groups such as the products sold under the names "GP 72 A" and "GP 71" from Genesee;

alkoxylated groups such as the product sold under the name "Silicone Copolymer F-755" by SWS Silicones and Abil Wax 2428, 2434 and 2440 by the company Goldschmidt;

hydroxylated groups such as the polyorganosiloxanes containing a hydroxyalkyl function, described in French patent application FR-A-85 16334;

acyloxyalkyl groups such as, for example, the polyorganosiloxanes described in patent US-A-4 957 732;

anionic groups of carboxylic type, such as, for example, in the products described in patent EP 186 507 from the company Chisso Corporation, or of alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names "Abil® S201" and "Abil® S255";

hydroxyacylamino groups, such as the polyorganosiloxanes described in patent application EP 342 834. Mention may be made, for example, of the product Q2-8413 from the company Dow Corning.

The silicones as described above may be used alone or as a mixture, in an amount of between 0.01% and 20% by weight and preferably between 0.1% and 5% by weight relative to the total weight of the composition.

The composition according to the invention may comprise one or more plant oils such as sweet almond oil, avocado oil, castor oil, olive oil, jojoba oil, sunflower oil, wheatgerm oil, sesame seed oil, groundnut oil, grapeseed oil, soybean oil, rapeseed oil, passionflower oil, coconut oil, maize oil, hazelnut oil, shea butter, palm oil, apricot kernel oil or beauty-leaf oil, and mixtures thereof.

The term "cosmetically acceptable aqueous medium" means a medium that is compatible with keratin materials especially such as the skin, the eyelashes and the hair.

The cosmetically acceptable medium may consist solely of water or of a mixture of water and a cosmetically acceptable solvent, such as a $C_1$–$C_4$ lower alcohol, for instance ethanol, isopropanol, tert-butanol or n-butanol; alkylene glycols, for instance propylene glycol, polyol ethers; $C_5$–$C_{10}$ alkanes; acetone, methyl ethyl ketone; $C_1$–$C_4$ alkyl acetates, for instance methyl acetate, ethyl acetate or butyl acetate; dimethoxyethane, diethoxyethane; and mixtures thereof.

Preferably, the composition comprises from 50% to 95% by weight of water relative to the total weight of the composition.

The washing compositions according to the invention have a final pH generally of between 3 and 10. This pH is preferably between 5 and 8. The pH may be adjusted to the desired value in a conventional manner by adding a base (organic or mineral base) to the composition, for example aqueous ammonia or a primary, secondary or tertiary (poly) amine, for instance monoethanolamine, diethanolamine, triethanolamine, isopropanolamine or 1,3-propanediamine, or alternatively by adding an acid, preferably a carboxylic acid such as, for example, citric acid.

The compositions in accordance with the invention may contain, in addition to the combination defined above, viscosity regulators such as electrolytes, or thickeners (associative or nonassociative thickeners). Mention may be made in particular of sodium chloride, sodium xylenesulfonate, scleroglucans, xanthan gums, fatty acid alkanolamides, alkyl ether carboxylic acid alkanolamides optionally oxyethylenated with up to 5 mol of ethylene oxide, such as the product sold under the name "Aminol A15" by the company Chem Y, crosslinked polyacrylic acids and crosslinked acrylic acid/$C_{10}$–$C_{30}$ alkyl acrylate copolymers. These viscosity regulators are used in the compositions according to the invention in proportions that may be up to 10% by weight relative to the total weight of the composition.

The compositions in accordance with the invention may also preferably contain up to 5% of nacreous agents or opacifiers that are well known in the prior art, such as, for example, C16 higher fatty alcohols, fatty-chain acyl derivatives such as ethylene glycol or polyethylene glycol monostearate or distearate, and (C10–C30) fatty-chain ethers such as, for example, distearyl ether or 1-(hexadecyloxy)-2-octadecanol.

The compositions in accordance with the invention may also optionally contain at least one additive chosen from foam synergists such as $C_{10}$–$C_{18}$ 1,2-alkanediols or fatty alkanolamides derived from monoethanolamine or diethanolamine, silicone-based or non-silicone-based sunscreens, cationic polymers other than those of the invention, anionic or nonionic or amphoteric polymers other than those of the invention, proteins, protein hydrolyzates, ceramides, pseudoceramides, fatty acids containing linear or branched $C_{12}$–$C_{40}$ chains, such as 18-methyleicosanoic acid, hydroxy acids, vitamins, provitamins such as panthenol, animal, mineral or synthetic oils and any other additive conventionally used in cosmetics that does not affect the properties of the composition according to the invention.

The washing compositions according to the invention may obviously also contain any common adjuvant encountered in the field of shampoos, for instance fragrances, preserving agents, sequestering agents, softeners, dyes, moisturizers, antidandruff agents or antiseborrheic agents, and the like.

Needless to say, a person skilled in the art will take care to select this or these optional additional compound(s) and/or the amounts thereof such that the advantageous properties intrinsically associated with the combination in accordance with the invention are not, or are not substantially, adversely affected by the envisaged addition(s).

The compositions may be in the form of more or less thickened liquids, creams or gels, and they are mainly suitable for washing, caring for and/or styling the hair. They may also be in the form of rinse-out lotions.

The present invention also relates to a cosmetic process for treating keratin materials, which consists in applying an effective amount of a composition as described above to the keratin materials, and rinsing it out after an optional leave-in time.

According to one preferred embodiment of the invention, the composition may be used as a shampoo.

When the compositions in accordance with the invention are used as standard shampoos, they are simply applied to wet hair and the lather generated by massaging or rubbing with the hands is then removed, after an optional leave-in time, by rinsing with water, the operation possibly being repeated one or more times.

Concrete, but in no way limiting, examples illustrating the invention will now be given.

EXAMPLE 1

A shampoo composition in accordance with the invention was prepared:

| | |
|---|---|
| Sodium lauryl ether sulfate (70/30 C12/C14) containing 2.2 mol of ethylene oxide, at a concentration of 26% AM (AM = active material) | 14.7 g AM |
| Cocoylbetaine at a concentration of 30% AM | 6 g AM |
| Copolymer of dimethyldiallylammonium chloride and of acrylamide as an aqueous solution at a concentration of 8% AM (Merquat ® 550 from Nalco) | 0.4 g AM |
| pH agent qs | pH 7 |
| Acrylic copolymer as an aqueous emulsion at a concentration of 55% Carbotac ® XPD-1811 from Noveon | 5.5 g |
| Water qs | 100 g |

Hair treated with this shampoo shows good styling and volumizing properties.

The invention claimed is:

1. A composition for treating keratin materials comprising, in a cosmetically acceptable aqueous medium;

(a) at least two polymers, said polymers comprising; at least one adhesive polymer with a glass transition temperature of less than −20° C., and at least one polymer selected from the group consisting of cationic and amphoteric polymers comprising at least one cationic dialkyldiallylammonium monomer, and (b) at least one detergent surfactant.

2. The composition of claim 1, wherein the at least one detergent surfactant is chosen from anionic, amphoteric, nonionic and zwitterionic surfactants, and mixtures thereof.

3. The composition of claim 1, wherein said at least one detergent surfactant is present in an amount ranging from 4% to 50% by weight relative to the total weight of the composition.

4. The composition of claim 3, wherein said at least one detergent surfactant is present in an amount ranging from 8% to 25% by weight relative to the total weight of the composition.

5. The composition of claim 1, wherein the at least one adhesive polymer has a glass transition temperature ranging from −100° C. less than to −20° C.

6. The composition of claim 1, wherein the at least one adhesive polymer has a maximum tensile force Fmax of greater than 2 N.

7. The composition of claim 6, wherein the at least one adhesive polymer has a maximum tensile force Fmax ranging from 5 N to 100 N.

8. The composition of claim 1, wherein the at least one adhesive polymer is an acrylic acid copolymer.

9. The composition of claim 8, wherein the at least one adhesive polymer is a copolymer of acrylic acid, of acrylamide, of ethyl acrylate and of acrylonitrile.

10. The composition of claim 1, wherein the at least one adhesive polymer is present in an amount ranging from 0.05% to 20% by weight relative to the total weight of the composition.

11. The composition of claim 10, wherein the at least one adhesive polymer is present in an amount ranging from 0.01% to 10% by weight relative to the total weight of the composition.

12. The composition of claim 11, wherein the at least one adhesive polymer is present in an amount ranging from 0.05% to 5% by weight relative to the total weight of the composition.

13. The composition of claim 1, wherein said at least one polymer comprising at least one cationic dialkldiallylammonium monomer is from homopolymers and copolymers comprising, as chain constituents, at least one unit corresponding to formula (4a) or (4b):

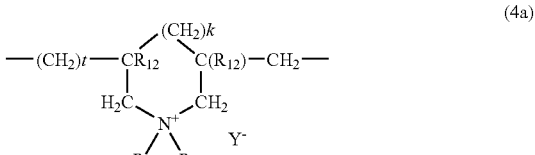

(4a)

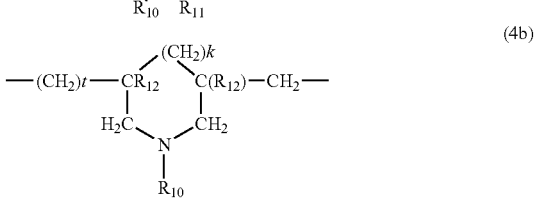

(4b)

wherein k and t are equal to 0 or 1, the sum k+t being equal to 1;

$R_{12}$ denotes a hydrogen atom or a methyl group;

$R_{10}$ and $R_{11}$, independently of each other, are chosen from alkyl groups containing from 1 to 8 carbon atoms, hydroxyalkyl groups, or lower ($C_1$–$C_4$) amidoalkyl groups, or alternatively $R_{10}$ and $R_{11}$ may form, together with the nitrogen atom to which they are attached, heterocylic groups;

$Y^-$ is an anion chosen from bromide, chloride, acetate, borate, citrate, tartrate, bisulfate, bisulfite, sulfate and phosphate.

14. The composition of claim 13, wherein in the definition of $R_{10}$ and $R_{11}$, the hydroxyalkyl groups comprise from 1 to 5 carbon atoms.

15. The composition of claim 13, wherein the heterocyclic groups are chosen from piperidyl and morpholinyl groups.

16. The composition of claim 13, wherein said at least one polymer comprising at least one cationic dialkyldiallylammonium monomer is chosen from copolymers of a dimethyldiallylammonium salt and of acrylamide, copolymers of dimethyldiallylammonium salt and of acrylic acid and homopolymers of dimethyldiallylammonium salts.

17. The composition of claim 1, wherein said at least one polymer comprising at least one cationic dialkyldiallylammonium monomer is present in an amount ranging from 0.001% to 10% by weight relative to the total weight of the composition.

18. The composition of claim 1, wherein the composition further comprises a silicone.

19. The composition of claim 18, wherein the silicone is present in an amount ranging from 0.01% to 20% by weight relative to the total weight of the composition.

20. The composition of claim 19, wherein the silicone is present in an amount ranging from 0.01% to 5% by weight relative to the total weight of the composition.

21. The composition of claim 1, wherein the pH of the composition ranges from 3 to 10.

22. A method for treating keratin materials, comprising applying to said keratin materials, a composition comprising, in a cosmetically acceptable aqueous medium;

(a) at least two polymers, said polymers comprising; at least one adhesive polymer with a glass transition temperature of less than −20° C., and at least one polymer selected from the group consisting of cationic and amphoteric polymers comprising at least one cationic dialkyldiallylammonium monomer, and (b) at least one detergent surfactant.

23. The method of claim 22, wherein treating keratin materials comprises cleansing, caring for, conditioning or styling the keratin materials.

24. The method of claim 22, wherein the method of treating keratin materials simultaneously cleans, conditions and styles the keratin materials.

25. A method for providing an improved styling effect to keratin materials, comprising applying to said keratin materials, a composition comprising, in a cosmetically acceptable aqueous medium;

(a) at least two polymers, said polymers comprising; at least one adhesive polymer with a glass transition temperature of less than −20° C., and at least one polymer selected from the group consisting of cationic and amphoteric polymers comprising at least one cationic dialkyldiallylammonium monomer, and (b) at least one detergent surfactant.

* * * * *

UNITED STATES PATENT AND TRADEMARK OFFICE
CERTIFICATE OF CORRECTION

PATENT NO. : 7,179,770 B2 Page 1 of 1
APPLICATION NO. : 10/499019
DATED : February 20, 2007
INVENTOR(S) : Béatrice Perron and Serge Restle It is certified that error appears in the above-identified patent and that said Letters Patent is hereby corrected as shown below:

In claim 5, column 12, line 21, "-100° C. less than to -20° C." should read -- -100° C. to less than -20° C.--.

In claim 11, column 12, line 40, "0.01%" should read --0.1%--.

In claim 12, column 12, line 44, "0.05%" should read --0.5%--.

In claim 13, column 12, line 48, "is from" should read --is chosen from--.

In claim 20, column 13, line 35, "0.01%" should read --0.1%--.

Signed and Sealed this

Twenty-fourth Day of April, 2007

JON W. DUDAS
*Director of the United States Patent and Trademark Office*